US010688171B2

(12) United States Patent
Cherpes et al.

(10) Patent No.: US 10,688,171 B2
(45) Date of Patent: Jun. 23, 2020

(54) ***CHLAMYDIA*-ACTIVATED B CELL PLATFORMS AND METHODS THEREOF**

(71) Applicant: OHIO STATE INNOVATION FOUNDATION, Columbus, OH (US)

(72) Inventors: Thomas Cherpes, Columbus, OH (US); Rodolfo Vicetti Miguel, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/550,110

(22) PCT Filed: Feb. 10, 2016

(86) PCT No.: PCT/US2016/017338
§ 371 (c)(1),
(2) Date: Aug. 10, 2017

(87) PCT Pub. No.: WO2016/130667
PCT Pub. Date: Aug. 18, 2016

(65) Prior Publication Data

US 2018/0028642 A1 Feb. 1, 2018

Related U.S. Application Data

(60) Provisional application No. 62/114,349, filed on Feb. 10, 2015, provisional application No. 62/247,827, filed on Oct. 29, 2015.

(51) Int. Cl.
*A61K 39/002* (2006.01)
*A61K 39/118* (2006.01)
*C12N 5/0781* (2010.01)
*A61K 39/00* (2006.01)

(52) U.S. Cl.
CPC .......... *A61K 39/118* (2013.01); *C12N 5/0635* (2013.01); *A61K 2039/5154* (2013.01); *A61K 2039/58* (2013.01); *A61K 2039/6006* (2013.01); *C12N 2500/72* (2013.01); *C12N 2502/70* (2013.01)

(58) Field of Classification Search
None
See application file for complete search history.

(56) References Cited

U.S. PATENT DOCUMENTS

| | | | |
|---|---|---|---|
| 5,759,551 | A | 6/1998 | Ladd et al. |
| 5,843,446 | A | 12/1998 | Ladd et al. |
| 6,001,372 | A | 12/1999 | DeMars et al. |
| 6,465,251 | B1 | 10/2002 | Schultze et al. |
| 6,653,461 | B2 | 11/2003 | DeMars et al. |
| 7,851,609 | B2 | 12/2010 | Jackson |
| 7,964,200 | B2 | 6/2011 | Mrsny et al. |
| 8,309,102 | B2 | 11/2012 | Mrsny et al. |
| 8,318,906 | B2 | 11/2012 | Braun et al. |
| 2002/0072093 | A1 | 6/2002 | Chen et al. |
| 2002/0142001 | A1 | 10/2002 | Brunham |
| 2003/0118569 | A1 | 6/2003 | Bankert |
| 2006/0121055 | A1 | 6/2006 | Campbell |
| 2006/0234260 | A1 | 10/2006 | Griffais et al. |
| 2009/0022755 | A1 | 1/2009 | Barth et al. |
| 2013/0345277 | A1 | 12/2013 | Wandinger-Ness et al. |
| 2014/0275478 | A1 | 9/2014 | Follmann et al. |

FOREIGN PATENT DOCUMENTS

| | | |
|---|---|---|
| DE | 19954514 | 5/2001 |
| WO | 1999015157 | 9/1999 |
| WO | 2001034194 | 5/2001 |
| WO | 2007126163 | 11/2007 |
| WO | 2010149394 | 12/2010 |
| WO | 2013049941 | 4/2013 |
| WO | 2014153087 A1 | 9/2014 |
| WO | 2015016718 | 2/2015 |
| WO | 2016130667 | 8/2016 |

OTHER PUBLICATIONS

Zhu, et al., "Identification of immunodominant linear B-cell epitopes within the major outer membrane protein of Chlamydia trachomatis", Acta Biochim Biophys Sin (2010): 1-8.

Hua, et al., "Immunogenicity of a chimeric peptide corresponding to T helper and B Cell Epitopes of the Chlamidia trachomatis major outer membrane protein", J of Experim Med 175 (1992), 227-235.

International Preliminary Report on Patentability issued in Application No. PCT/US2016/017338, dated Aug. 27, 2017.

International Search Report and Written Opinion issued in Application No. PCT/US2016/017338, dated May 6, 2016.

Wortis, et al., "B-Cell activation by crosslinking of surface IgM or litigation of CD40 involves alternative signal pathways and results in different B-Cell phenotypes", Proc. Natl. Acad. Sci. USA 92 (1995), 3348-3352.

Massari, et al., "Toll-Like Receptor 2-Dependent Activity of Native Major Outer Membrane Protein Proteosomes of Chlamydia trachomatis", Infection and Immunity 81 (2013), 303-310.

Peterson, et al., "Split tolerance of Th1 and Th2 cells in tolerance to Theiler's murine encephalomyelitis virus", Eur. J. Immunol. 23 (1993), 46-55.

Soldera, et al., "Selective down-regulation of Th2 immune responses following treatment with antigen-coupled splenocytes", Eur. J. Immunol. 27 (1997), 848-54.

(Continued)

*Primary Examiner* — Jennifer E Graser
(74) *Attorney, Agent, or Firm* — Meunier Carlin & Curfman LLC

(57) ABSTRACT

Disclosed herein is a *Chlamydia*-activated B cell (CAB) platform. Also disclosed is a method of enhancing a population of B cells, comprising exposing said B cells to *Chlamydia* spp. under conditions suitable to enhance the population of B cells, such that expansion and differentiation of said B cells takes place, and said B cells are exposed or crosslinked to an antigen. Also disclosed are methods of producing said CABs, and treating a subject in need thereof with said CABs.

6 Claims, 12 Drawing Sheets

(56) References Cited

OTHER PUBLICATIONS

Toussi, et al., "Immune Adjuvant Effect of Molecularly-defined Toll-Like Receptor Ligands", Vaccines 2, (2014), 323-353.

Houston et al., "Protein engineering of antibody binding sites: Recovery of specific activity in an anti-digoxin single-chain Fv analogue produced in *Escherichia coli*", Proc. Natl. Acad. Sci. USA (1988), 85:5879-5883.

Bird et al., "Single-chain antigen-binding proteins", Science 242 (1988), 423-426.

Heinz et al. Comprehensive in silico Prediction and Analysis of Chlamydial Outer Membrane Proteins Reflects Evolution and Lifestyle of the Chlamydiae. BMC Genomics. (2009), 10:634.

Fluckiger, et al., "In Vitro Reconstitution of Human B-Cell Ontogeny: From CD341Multipotent Progenitors to Ig-Secreting Cells", Blood 1998 92: 4509-4520.

Luo, et al., "Engineering human hematopoietic stem/progenitor cells to produce a broadly neutralizing anti-HIV antibody after in vitro maturation to human B lymphocytes", Blood 2009, 113, 1422-1431.

Arch, et al., "Tumor necrosis factor receptor-associated factors (TRAF5)—a family of adapter proteins that regulates life and death", Genes Dev. 12 (1998), pp. 2821-2830.

Noelle et al., "Cognate interactions between helper T cells and B cells. V. Reconstitution of T helper cell function using purified plasma membranes from activated Th1 and Th2 T helper cells and lymphokines.", J. Immunol. 146 (1991), 1118-1124.

European Patent Office. Extended European Search Report. Issued in European Application No. 16749794.0 dated Jun. 11, 2018. 6 pages.

Levitt, D., R. Danen, and J. Bard. "Both species of chlamydia and two biovars of Chlamydia trachomatis stimulate mouse B lymphocytes." The Journal of Immunology 136.11 (1986): 4249-4254.

European Patent Office. Communication pursuant to Aritcle 94(3) EPC. Issued in European Application No. 16749794.0 dated Jan. 30, 2019. 4 pages.

Communication Pursuant to Article 94(3) EPC issued for European Application No. 16749794, dated Nov. 6, 2019.

XP55637029A—Bard, et al., "Chlamydia trachomatis stimulates human peripheral blood B lymphocytes to proliferate and secrete polyclonal immunoglobulins in vitro." Infection and immunity 43.1 (1984): 84-92.

Office Action issued for Japanese Application No. 2017-541938, dated Dec. 17, 2019.

International Search Report and Written Opinion issued by the International Searching Authority (ISA/US) in PCT Application No. PCT/US2018/024007 dated Aug. 2, 2019. 18 pages.

Findlay, Heather E., Heather McClafferty, and Richard H. Ashley. "Surface expression, single-channel analysis and membrane topology of recombinant Chlamydia trachomatis Major Outer Membrane Protein." BMC microbiology 5.1 (2005): 5.

GenBank Accession No. DQ064295. Chlamydia trachomatis strain L2/434 major outer membrane protein (*ompA*) gene, complete cds. Jan. 26, 2006.

Stephens, Richard S., et al. "Sequence analysis of the major outer membrane protein gene from Chlamydia trachomatis serovar L2." Journal of bacteriology 168.3 (1986): 1277-1.

Cambridge MedChem Consulting, Formulation, 2012. 5 pages. Available on-line at www.cambridgemedchemconsulting.com/resources/formulation.html.

Office Action issued in U.S. Appl. No. 15/775,155, dated Mar. 25, 2020.

*CHLAMYDIA*-ACTIVATED B CELL PLATFORMS AND METHODS THEREOF

CROSS-REFERENCE TO RELATED APPLICATIONS

This application is a national stage application filed under 35 U.S.C. § 371 of PCT/US2016/017338 filed Feb. 10, 2016, which claims benefit of U.S. Provisional Application No. 62/114,349, filed Feb. 10, 2015, and U.S. Provisional Application No. 62/247,827, filed Oct. 29, 2015, both of which are hereby incorporated herein by reference in their entirety.

BACKGROUND

Dendritic cells (DCs) are considered potent antigen-presenting cells (APCs), and are effective inducers of protective immunity against infectious diseases and cancer. These have prompted intense interest in the use of DCs as cellular vaccines; especially DCs differentiated form peripheral blood monocytes. However, clinical trials using DCs have only demonstrated very low rates of overall clinical response, highlighting the need to improve DC-based vaccines. Particular restrictions for the success of these cellular therapies have been the limited number of DCs that can be produced from monocytes, as DC cannot be expanded ex vivo, making it difficult to generate large numbers of these cells for use in long-term, multi-administration protocol. Moreover, DCs have a significant degree of variability in their ability to prime immune responses after cryopreservation. These limitations becomes especially important because greater DC numbers and treatments have been shown to elicit more robust antitumor immunity and improve clinical responses.

B cells represent a large pool of potent APCs, and are likely the only autologous APCs alternative to DC that can be generated ex vivo for immunotherapeutic purposes. While B cells have been described to induce T cell tolerance or even to block antitumor immune responses in vivo, these reports were restricted to resting B cells lacking important accessory and costimulatory molecules expression. On the other hand, B cells can be activated to become effective APCs by cells expressing CD40L in combination with cytokines or Toll-like receptor (TLR) ligands, however these approaches either did not induce optimal B cell activation (TLR ligands) or required the use of cell lines (CD40L), and these limitations make them unsuitable for clinical application.

Activated B cells have enhanced MHC and costimulatory molecules expression, and exhibit greatly improved antigen presentation capacity to fully activate naïve and memory T cells. Also of importance, activated B cells can recruit T cells through the secretion of chemokines and migrate to secondary lymphoid organs; critical requirements for in vivo induction of effective antitumor immune responses. Because B cells can be easily obtained ex vivo, they represent an attractive source of autologous APCs for immunotherapeutic applications. Moreover, activated B cells express MHC class I and II, and therefore be used with a wide range of antigens. Hence, a practical method that induces activation and proliferation of B cells is needed in the art to provide a cellular vaccine to target multiple types of tumors and infectious diseases.

SUMMARY

Disclosed herein is a platform for creating activated, antigen-presenting cells (APCs), wherein the platform comprises: a) *Chlamydia* spp. (including *C. trachomatis, C. psittaci* and *C. muridarum*), or an activating protein, peptide, or fragment thereof; b) a population of B cells; and c) an antigen, wherein the antigen is not derived from *Chlamydia* spp. (including *C. trachomatis. C. psittaci* and *C. muridarum*), or from a protein, peptide, or fragment thereof.

Also disclosed is a method for producing activated, antigen-presenting *Chlamydia*-activated B cells in a subject, the method comprising: a) obtaining B-cells from a subject; b) exposing the B cells from step a) to *Chlamydia* spp. (including C. spp. (including *C. trachomatis. C. psittaci* and *C. muridarum*), or an activating protein, peptide, or fragment thereof; c) exposing the B cells of step b) to a desired antigen, wherein the antigen is not derived from C. spp. (including *C. trachomatis, C. psittaci* and *C. muridarum*), or from a protein, peptide, or fragment thereof, thereby obtaining activated, antigen-presenting *Chlamydia*-activated B cells (CABs).

Also disclosed is a method of treating a subject in need thereof, the method comprising: a) obtaining B cells from the subject; b) exposing the B cells from step a) to *Chlamydia* spp. (including *C. trachomatis. C. psittaci* and *C. muridarum*), or an activating protein, peptide, or fragment thereof; c) exposing the B cells of step b) to an antigen, wherein the antigen is not derived from *Chlamydia* spp. (including *C. trachomatis, C. psittaci* and *C. muridarum*), or from a protein, peptide, or fragment thereof, thereby obtaining activated, antigen-presenting *Chlamydia*-activated B cells (CABs); and d) treating the subject with the activated, antigen-presenting *Chlamydia*-activated B cells of step c).

The details of one or more embodiments of the invention are set forth in the accompanying drawings and the description below. Other features, objects, and advantages of the invention will be apparent from the description and drawings, and from the claims.

Mice were then intravenously challenged with 200,000 B16-F10 cells. 18 days later, lung tumor nodules were enumerated. Left panel shows number of lung tumor nodules in mice treated with unloaded CABs or with CAB-B16; right panel shows representative results from both groups of treated mice.

Figure 1:
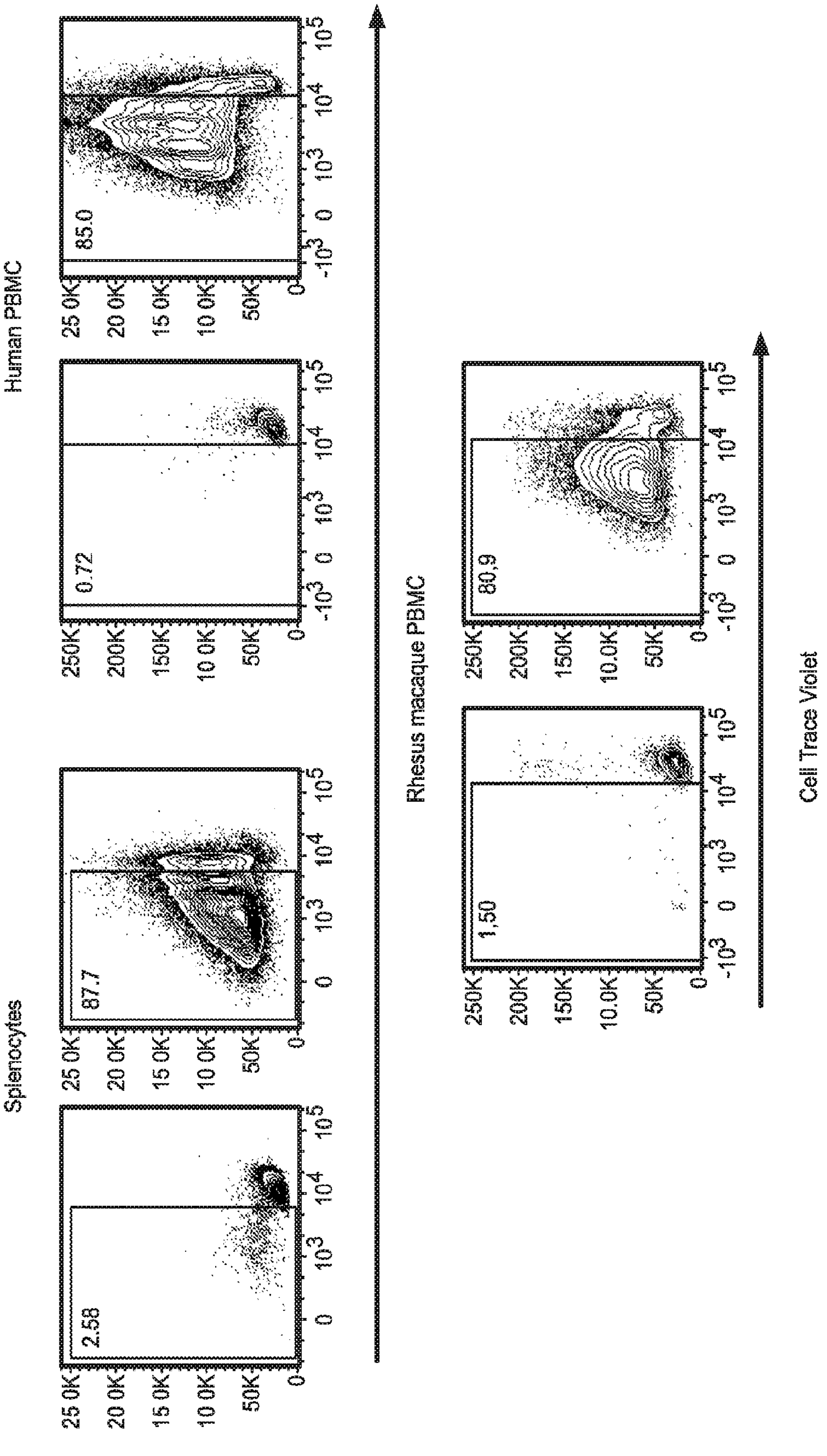
FIG. 1 shows a schematic of *C. trachomatis* activating mouse, macaque, and human B cells. CABs have also been generated in dogs and cats.
Figure 2:
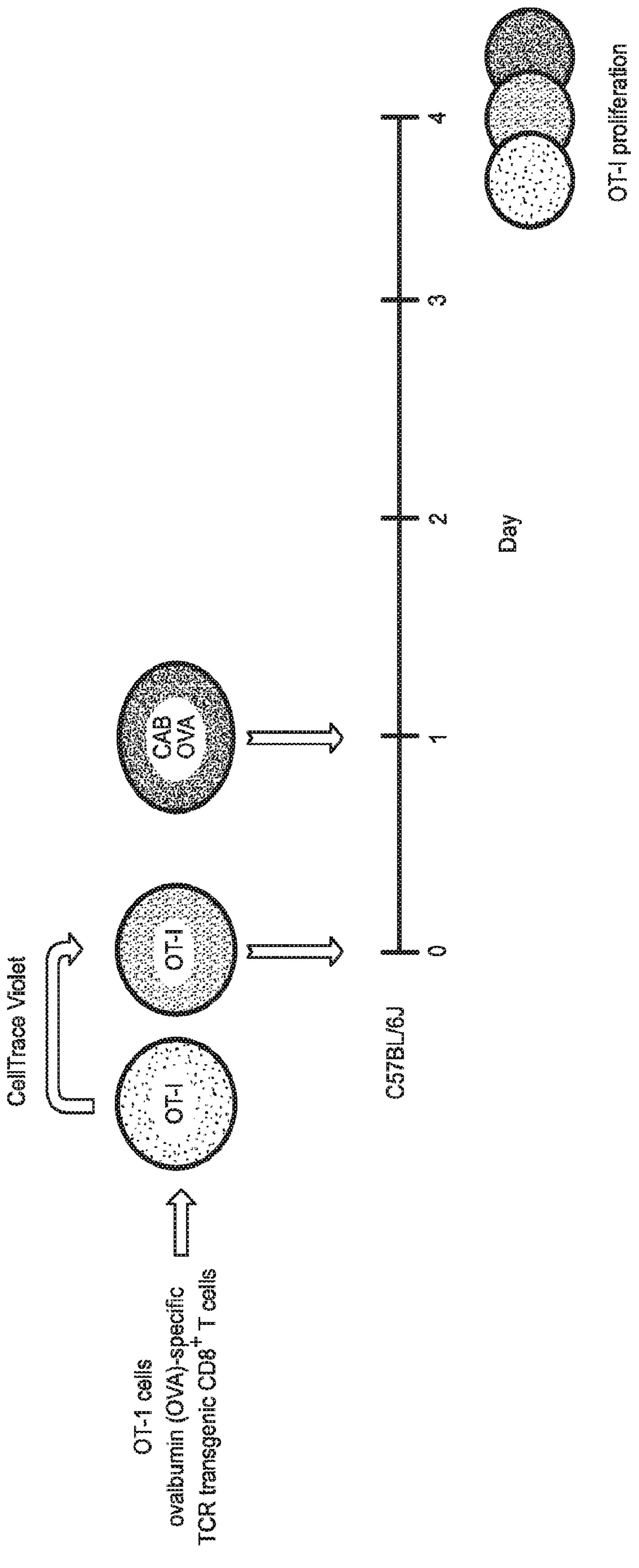
FIG. 2 shows a schematic depicting the experimental design used to demonstrate that CABs can cross-prime soluble antigens and activate antigen-specific CD8+ T cells. The T cell receptor (TCR) for transgenic OT-I mice are specific for ovalbumin (OVA), and these cells were acquired from the spleen, labeled with a fluorescent marker to determine cell proliferation, and then transferred into wild type mice 1 day prior to treatment of the wild type mice with CABs loaded with OVA. Proliferation of the OT-I cells was assessed after three days by flow cytometry.
Figure 3:
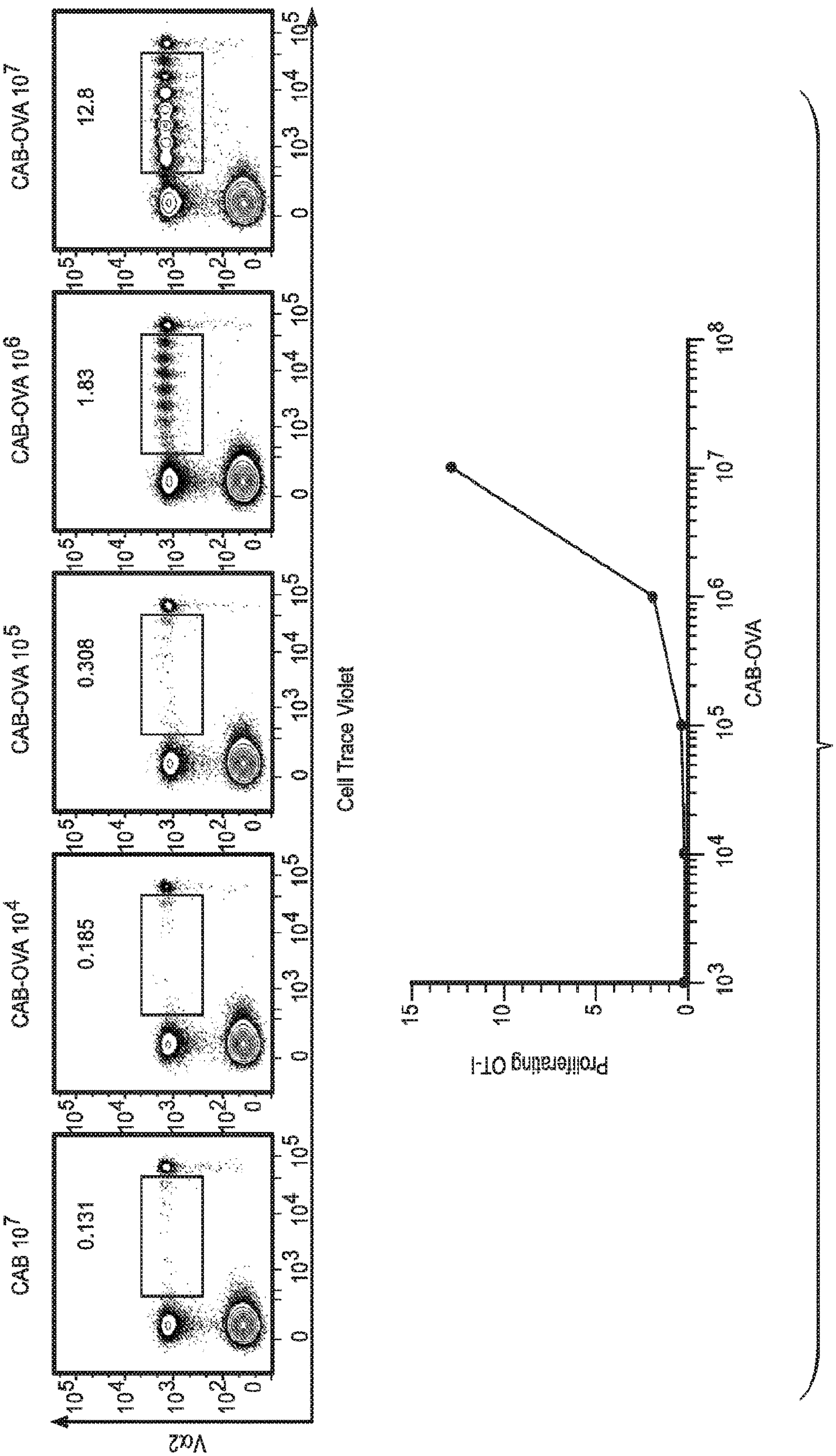
FIG. 3 shows that CABs can cross-prime antigen-specific CD8+ T cells in vivo in a dose-dependent manner.
Figure 4:
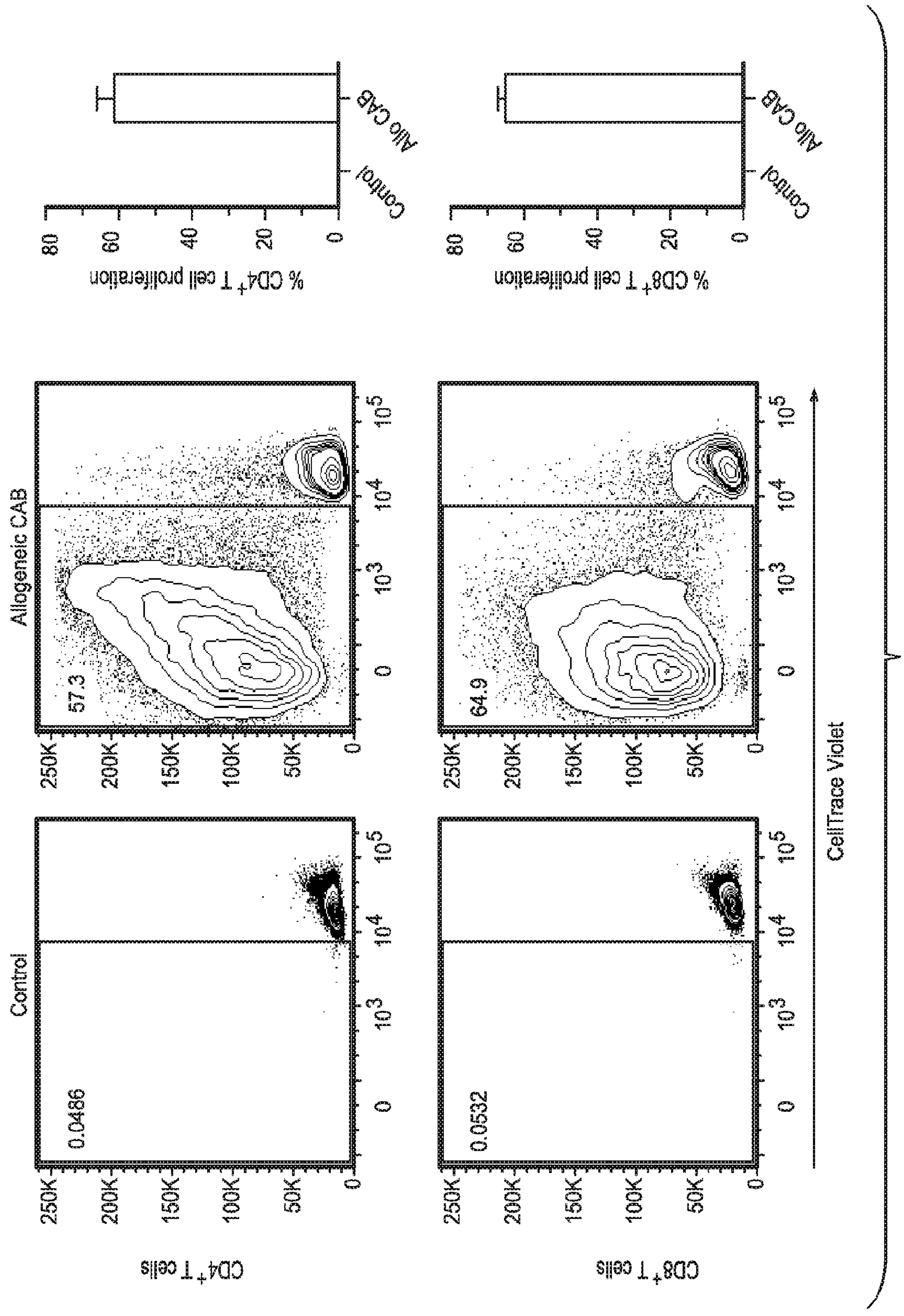
FIG. 4 shows human CABs promote robust allogeneic naïve T cell proliferation of both human naïve CD4+ and CD8+ T cells after 7 days in co-culture. Flow cytometry was used to assess the ability of CABs to induce T cell proliferation.
Figure 5:
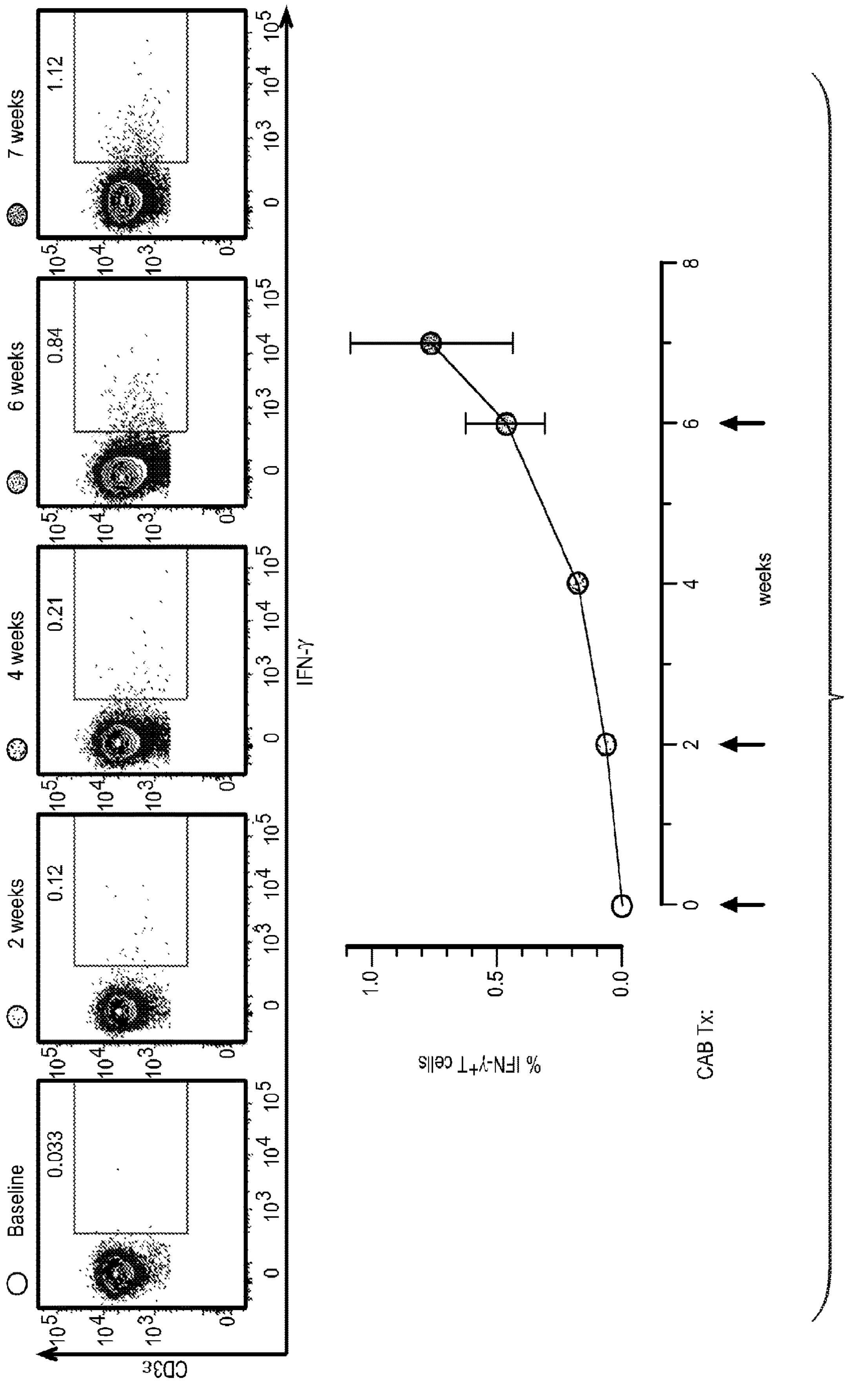
FIG. 5 shows rhesus macaques treated in vivo with CABs loaded with specific antigen at the indicated time points. PBMC from these animals were then used to assess antigen-specific T cell responses. CAB treatments greatly increased T cell secretion of interferon-gamma. In addition, there were no discernable adverse effects from these treatments.
Figure 6:
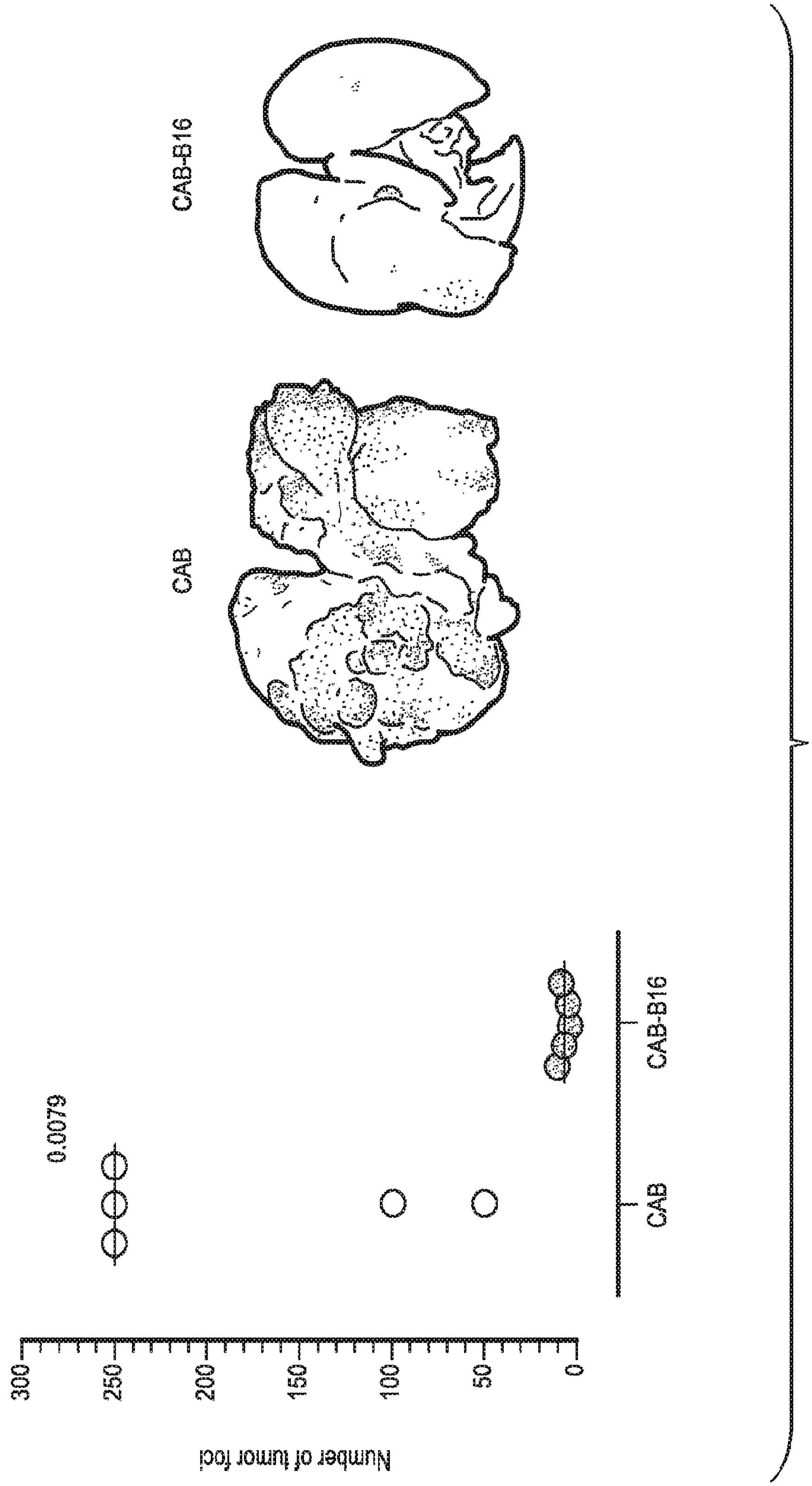
FIG. 6 shows C57BL/6J mice were vaccinated with unloaded CABs (CAB) or CABs loaded with B16 melanoma-specific peptides (Trp-2 and gp100) (i.e. CAB-B16).
Figure 7:
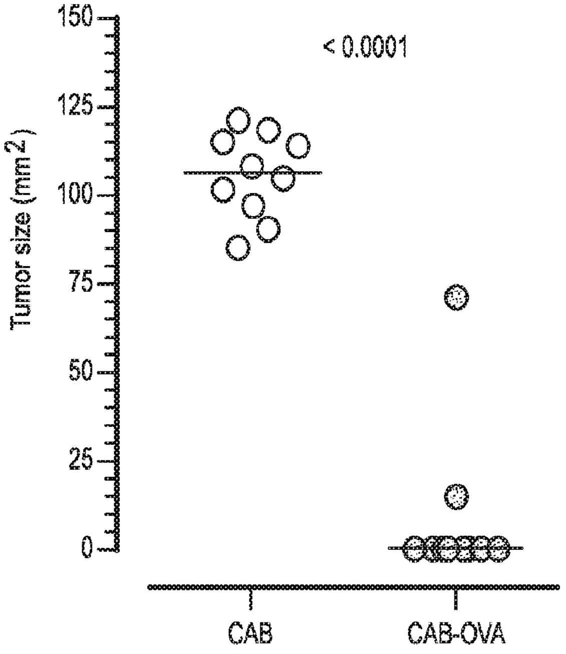

FIG. 7 shows CABs prime endogenous CTL responses with robust antitumor activity. OVA-specific CAB treatment prior to subcutaneous injection of E.G7-OVA tumor can prevent tumor development.

Figure 8:
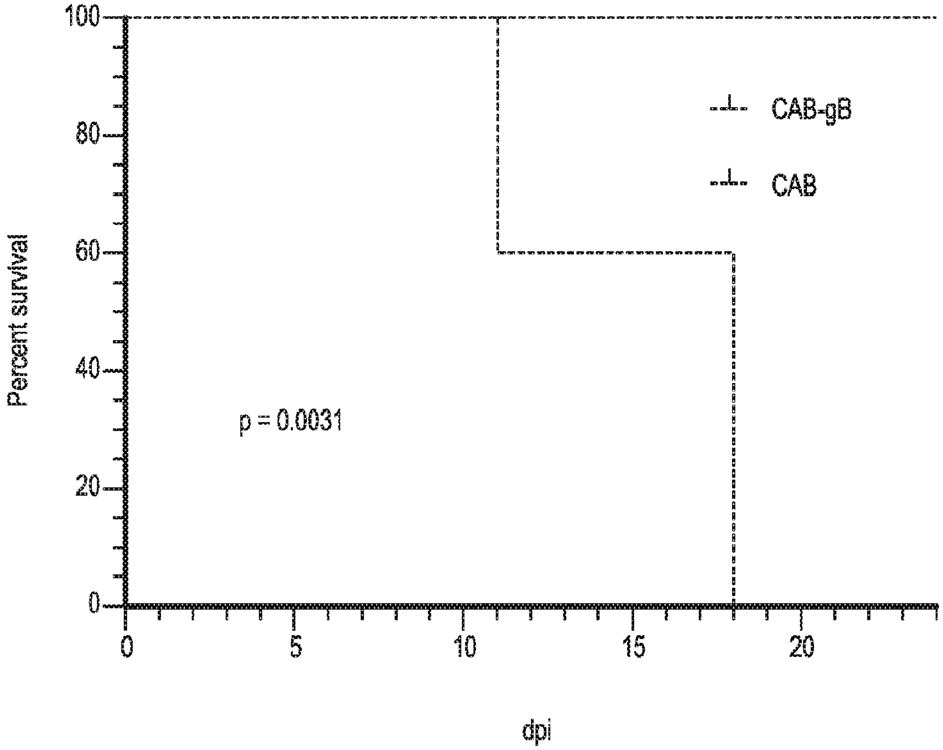

FIG. 8 shows CABs prime endogenous CTL responses with robust antiviral activity. CABs loaded with immunodominant epitope of HSV-1 ($gB_{498-505}$) prior to lethal ocular HSV-2 challenge rescued animals from lethal infection.

Figure 9:
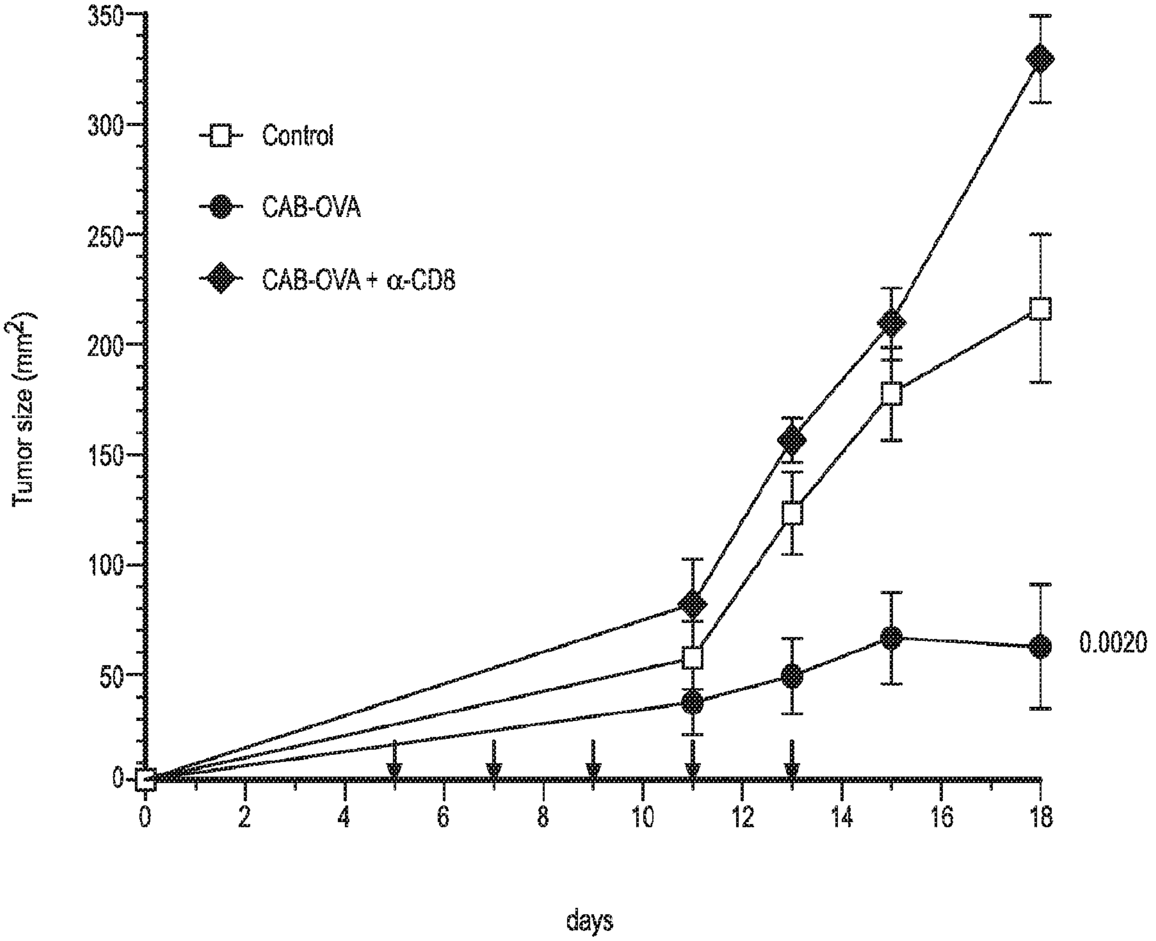

FIG. 9 shows OVA-loaded CABs control early-established tumor by promoting CTL immunity. CAB treatments were not administered until beginning 5 days after tumor injection. As displayed, antigen-specific CAB treatments significantly restricted tumor development, and this effect was abrogated when mice were treated with an antibody that depleted endogenous CD8 T cells. Blue arrows indicate CAB treatments.

Figure 10:
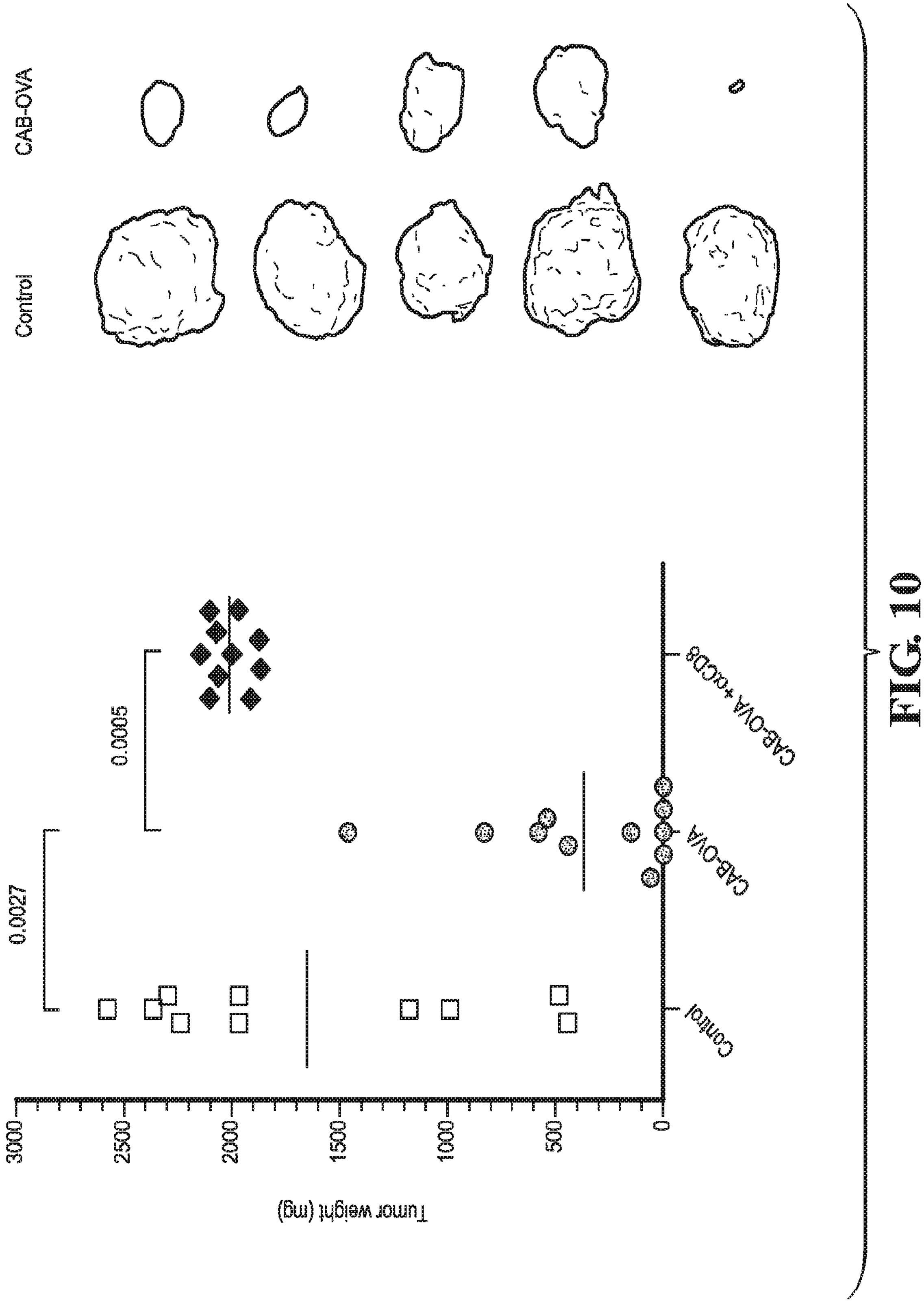

FIG. 10 shows OVA-loaded CABs control early established tumors. This accompanies the tumor growth results over time in shown in FIG. 9.

Figure 11:
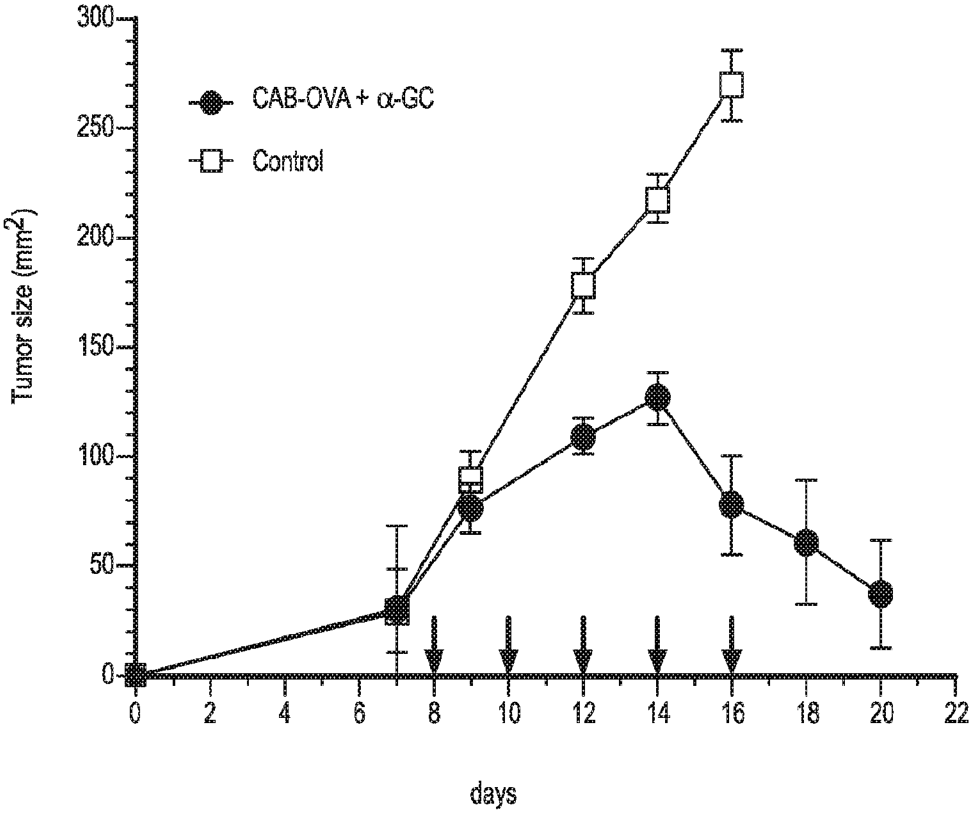

FIG. 11 shows αGC increases CAB therapeutic effectiveness. CABs were loaded with αGC prior to injection in an effort to optimize CAB efficacy. Because CABs and not mice were treated with αGC, this avoided toxicity associated with in vivo αGC administration. Blue arrows indicate CAB treatments.

Figure 12:
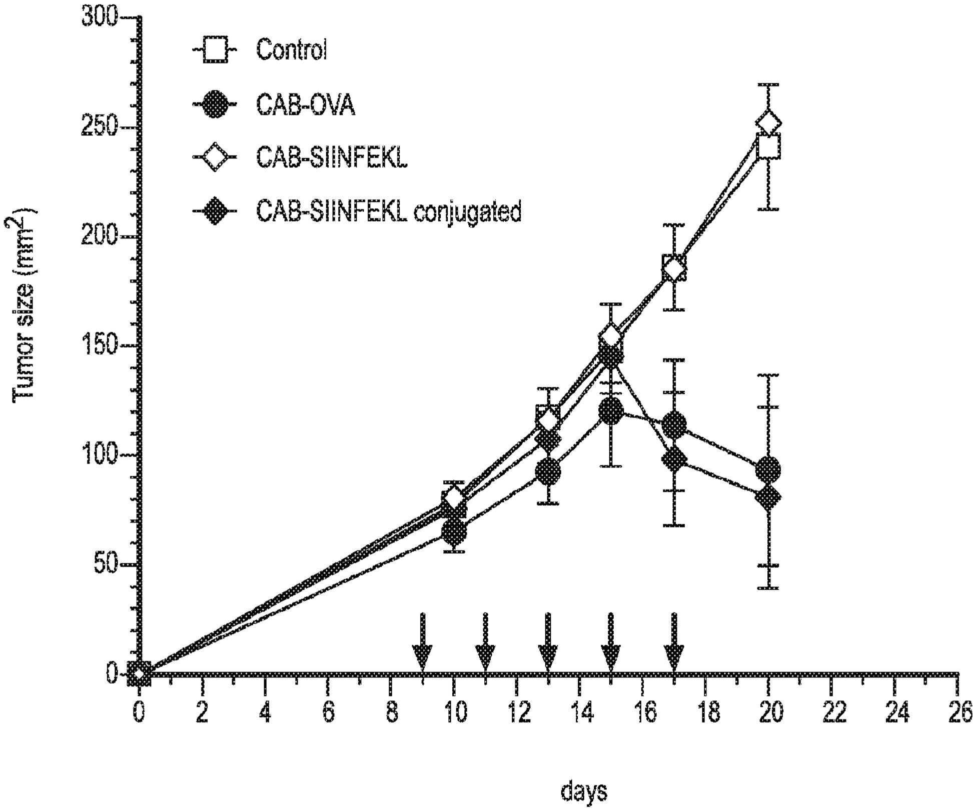

FIG. 12 shows crosslinking of immunodominant peptide of OVA (SIINFEKL) to CABs increases the consistency of their therapeutic efficacy. Zero-length crosslinking is performed using water-soluble 1-ethy 1-3-(3-dimethylaminopropy 1)-carbodiimide. Blue arrows indicate CAB treatments.

Figure 13:
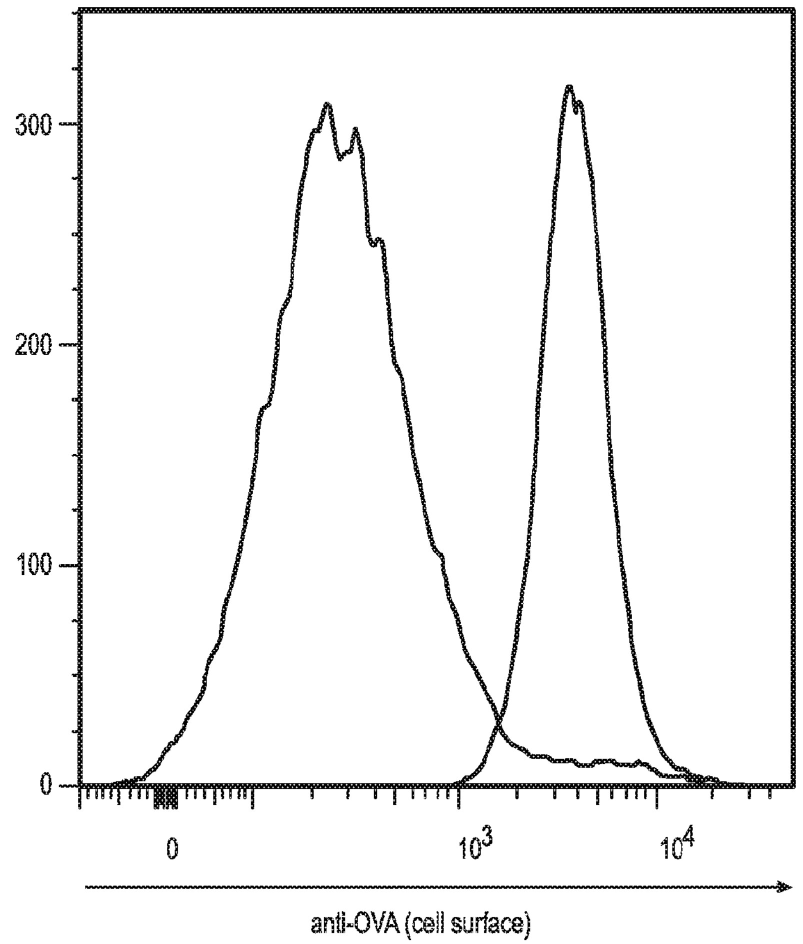

FIG. 13 shows an example of crosslinking an antigen (OVA) to CABs. The peak on the left side indicates CABs that underwent mock crosslinking, while the peak on the right side indicates CABs that were crosslinked with OVA. Detection of crosslinked OVA on the cell surface of CABs was performed with an anti-OVA monoclonal antibody.

DETAILED DESCRIPTION

Definitions

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of .+−.20% or .+−.10%, more preferably .+−.5%, even more preferably .+−.1%, and still more preferably .+−.0.1% from the specified value, as such variations are appropriate to perform the disclosed methods.

The term "antigenic composition" refers to a composition comprising material which stimulates the immune system and elicits an immune response in a host or subject.

The term "elicit an immune response" refers to the stimulation of immune cells in vivo in response to a stimulus, such as an antigen. The immune response consists of both cellular immune response, e.g., T cell and macrophage stimulation, and humoral immune response, e.g., B cell and complement stimulation and antibody production. Immune response may be measured using techniques well-known in the art, including, but not limited to, antibody immunoassays, proliferation assays, and others.

The term "vaccine" as used herein refers to a composition comprising a recombinant virus as described herein, which is useful to establish immunity to the virus in the subject. It is contemplated that the vaccine comprises a pharmaceutically acceptable carrier and/or an adjuvant. It is contemplated that vaccines are prophylactic or therapeutic.

A "prophylactic" treatment is a treatment administered to a subject who does not exhibit signs of a disease or exhibits only early signs for the purpose of decreasing the risk of developing pathology. The vaccines disclosed herein can be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms.

The signs or symptoms may be biochemical, cellular, histological, functional, subjective or objective.

The term "inactivated" is used herein to describe a microorganism, such as *Chlamydia* spp. (including *C. trachomatis, C. psittaci* and *C. muridarum*), that is also known in the art as a "killed" or "dead" microorganism. An inactivated bacterium is a whole bacterium without infective properties and is produced from a "live" bacterium, regardless of whether the bacterium has been previously attenuated in any manner.

A "fragment" of a polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies can be produced from the vaccines described herein, and may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means to reduce the frequency or severity of at least one sign or symptom of a disease or disorder.

An "effective amount" as used herein, means an amount which provides a therapeutic or prophylactic benefit.

As used herein, an "immunoassay" refers to any binding assay that uses an antibody capable of binding specifically to a target molecule to detect and quantify the target molecule.

As used herein, an "instructional material" includes a publication, a recording, a diagram, or any other medium of expression which can be used to communicate the usefulness of a compound, composition, method, platform, or system of the invention in the kit for practicing the methods described herein. The instructional material of the kit of the invention can, for example, be affixed to a container which contains the identified compound, composition, platform, or delivery system of the invention or be shipped together with a container which contains the identified compound, composition, method components, platform, or system of the invention. Alternatively, the instructional material can be shipped separately from the container with the intention that the instructional material and the compound be used cooperatively by the recipient.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The terms "tumor cell" or "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. The term "tumor-associated antigen" or "TAA" is used herein to refer to a molecule or complex which is expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules. Knowledge of the existence or characteristics of a particular tumor-associated antigen is not necessary for the practice of the invention.

The term "B cell" refers to a B lymphocyte. B cell precursors reside in the bone marrow where immature B cells are produced. B cell development occurs through several stages, each stage representing a change in the genome content at the antibody loci. In the genomic heavy chain variable region there are three segments, V, D, and J, which recombine randomly, in a process called VDJ rearrangement to produce a unique variable region in the immunoglobulin of each B cell. Similar rearrangements occur for the light chain variable region except that there are only two segments involved, V and J. After complete rearrangement, the B cell reaches the IgM+ immature stage in the bone marrow. These immature B cells present a membrane bound IgM, i.e., BCR, on their surface and migrate to the spleen, where they are called transitional B cells. Some of these cells differentiate into mature B lymphocytes. Mature B cells expressing the BCR on their surface circulate the blood and lymphatic system performing the role of immune surveillance. They do not produce soluble antibodies until they become fully activated. Each B cell has a unique receptor protein that will bind to one particular antigen. Once a B cell encounters its antigen and receives an additional signal from a T helper cell, it can further differentiate into either a plasma B cell expressing and secreting soluble antibodies, or a memory B cell.

The term "B cell" can also refer to any B lymphocyte which presents a fully rearranged, i.e., a mature, B cell receptor (BCR) on its surface. For example, a B cell can be an immature or a mature B cell and is preferably a naïve B cell, i.e., a B cell that has not been exposed to the antigen specifically recognized by the BCR on the surface of said B cell. The B cells can be memory B cells, preferably IgG+ memory B cells. The term "B cells" can also refer to a mixture of B cells. A mixture of B cells can mean that the B cells in the mixture have different antigen-specificities, i.e., produce antibodies or fully rearranged BCRs which recognize a variety of antigens. The antibodies or BCRs of a single B cell are usually identical, also with respect to antigen-specificity.

The term "B cells secreting antibodies" preferably refers to plasma B cells. The term "B cells carrying a BCR on their surface" preferably refers to B cells expressing a BCR, preferably a fully rearranged BCR, at their plasma membrane. In this context, "a BCR" preferably does not mean a single BCR but preferably means a multitude of BCRs having the same antigen.

The term "portion" refers to a fraction. A portion preferably means at least 20%, at least 30%, preferably at least 40%, preferably at least 50%, more preferably at least 60%, more preferably at least 70%, even more preferably at least 80%, and most preferably at least 90% of the entire entity. The term "substantial portion" preferably refers to at least 50%, more preferably at least 60%, more preferably at least 70%, even more preferably at least 80%, even more preferably at least 90%, even more preferably at least 95%, and most preferably at least 99% of the entire entity.

The term "clonal expansion" refers to a process wherein a specific entity is multiplied. In the context of the present invention, the term is preferably used in the context of an immunological response in which lymphocytes, preferably B lymphocytes, are stimulated by an antigen, proliferate, and the specific lymphocyte recognizing said antigen is amplified.

Preferably, clonal expansion leads to differentiation of the lymphocytes, preferably into lymphocytes producing and secreting antibodies. B lymphocytes secreting antibodies are, for example, plasma B cells.

The term "antigen" relates to an agent comprising an epitope against which an immune response is to be generated. The term "antigen" includes, in particular, proteins, peptides, polysaccharides, lipids, nucleic acids, especially RNA and DNA, and nucleotides. The term "antigen" also includes derivatized antigens as secondary substance which becomes antigenic—and sensitizing—only through transformation (e.g., intermediately in the molecule, by completion with body protein), and conjugated antigens which, through artificial incorporation of atomic groups (e.g., isocyanates, diazonium salts), display a new constitutive specificity. In a preferred embodiment, the antigen is a tumor antigen, i.e., a constituent of cancer cells which may be derived from the cytoplasm, the cell surface and the cell nucleus, in particular those antigens which are produced, preferably in large quantity, intracellularly or as surface antigens on tumor cells. Examples are carcinoembryonic antigen, a 1-fetoprotein, isoferritin and fetal sulfoglycoprotein, a2-H-ferroprotein and γ-fetoprotein and various viral tumor antigens. In a further embodiment, the antigen is a viral antigen such as viral ribonucleoproteins or envelope proteins. In particular, the antigen or peptides thereof should be recognizable by a B cell receptor or an immunoglobulin molecule such as an antibody. Preferably, the antigen if recognized by a B cell receptor is able to induce in presence of appropriate co-stimulatory signals, clonal expansion of the B cell carrying the BCR specifically recognizing the antigen and the differentiation of such B cells into antibody secreting B cells. An antigen can present in a repetitive organization, i.e., the antigen comprises more than one, preferably at least 2, at least 3, at least 4, up to 6, 10, 12 or more agents or epitopes against which an immune response is to be generated or against which the antibodies which are to be produced. Such repetitive antigen preferably is capable of binding to more than one antibody of the same specificity. In other words, such repetitive antigen comprises more than one epitope, preferably identical epitope, and thus is capable of "cross-linking" antibodies directed to said epitope. The more than one agents or epitopes may be covalently or non-covalently linked, wherein a covalent linkage may be by any chemical grouping such as by peptide linkages. An antigen can be a fusion molecule comprising a repetition of an antigen peptide or comprising different antigen peptides having a common epitope. In one preferred embodiment, said antigen peptides are linked by peptide linkers.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 1000% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

General

Disclosed herein is a novel platform to quickly and easily generate large numbers of activated antigen presenting cells (APCs), such as activated B cells, for use as a cellular vaccine that induces and boosts immune responses against tumors and pathogens. Importantly, the functionality of these cells is unaffected by long-term cold storage. Using this platform, animal (e.g., mouse, cat, dogs and rhesus macaques) and human B cells obtained from peripheral blood or secondary lymphoid organs can be activated and expanded in vitro for infusion into the original donor using a variety of administration protocols. The B cells can be obtained from and used in the same individual (autologous), or the B cells can be obtained from one individual and used in another individual (allogenic). These cells can be activated in vitro by culture of peripheral blood mononuclear cells or whole lymphoid organ cell preparations in the presence of inactivated *Chlamydia trachomatis* elementary bodies or lysate, inducing their activation and proliferation, which are further enhanced by additional factors, such as cytokines. The number of activated B cells can be expanded many fold from the initial number of B cells. For example, the number of activated B cells can be expanded by 2, 3, 4, 5, 6, 7, 8, 9, 10, 11, 12, 13, 14, 15, 16, 17, 18, 19, or 20-fold or more when compared to a control. It is shown herein that these cells are efficient APCs, capable of processing foreign protein antigens, presenting immunogenic peptides and stimulating allogeneic, naïve CD4+ and CD8+ T cells as well as naïve and memory antigen-specific CD8+ T cells. Additionally, antigens can be loaded by crosslinking to CABs to increase their therapeutic capacity.

Expanding the number of efficient APCs available for loading with cognizant antigens makes the process of producing autologous cellular vaccines more effective, since in vivo administration of these activated B cells primes robust CD8+ T cell responses, capable of rejecting tumors and controlling viral infection. Therefore, a cellular vaccine platform has been developed for use in immunotherapy of tumors and infectious diseases. This platform and associated method is less invasive, costly, and labor intensive that other currently available cellular vaccine options.

*Chlamydia trachomatis* has the unique ability to induce selective polyclonal activation of resting B cells, easily obtained from peripheral blood or secondary lymphoid organs (e.g., lymph nodes), as well as from a wide variety of mammals (mouse, cats, dogs, rhesus macaques and humans). Inactivated *Chlamydia trachomatis* elementary bodies (EB) or their lysates are able to activate resting B cells obtained from peripheral blood or secondary lymphoid organs and induce their proliferation. This allows for their numbers to be expanded by significant amounts, which are further enhanced by additional factors, such as cytokines. This makes their subsequent immunomagnetic selection quite efficient. These *Chlamydia trachomatis*-activated B cells (CABs) express high levels of costimulatory molecules, and are able to acquire soluble proteins and process them more efficiently than resting B cells. These requisites allow the generated CABs to be able to present antigens to T cells. The generated CABs can be used for autologous or allogenic infusion using various administration protocols, due to the ability of the platform to generate large numbers of APCs and the amenability of CABs to be cryopreserved and still maintain their full functionality as APCs.

Also disclosed is the use of CABs to induce antigen-specific T cells against tumors and intracellular pathogens for active or passive immunotherapy, immunomonitoring and research purposes. More specifically, disclosed herein are human, murine and rhesus macaques CABs that have the ability to perform functions as efficient APCs, capable of processing foreign protein antigens, presenting immunogenic peptides and stimulating allogeneic naïve CD4+ and CD8+ T cells, as wells as naïve and memory antigen-specific CD8+ T cells. These properties allow CABs to prime in vivo T cell responses, including those desirable in the treatment of cancer.

CABs produced under the conditions disclosed herein (such as those described in Example 1) can be combined with any desired antigen or combination of antigens, as well as with immunogenic peptides, by a variety of techniques known to those of skill in the art. CABs can be administered intravenously to the subject, for example. The magnitude of T cell proliferation and activation is dependent on the number of APCs to be administered. Due to the high number of cells that can be obtained with the methods disclosed herein. T cell responses induced by repeated administration of high numbers of CABs is greater than the ones induced by currently available preparation of DCs, because of their limited numbers. For example, the CABs disclosed herein can be pulsed with cognate tumor antigens or tumor-specific peptides and induce tumor-specific CD8+ T cells responses, capable of rejecting the corresponding tumor challenges in murine models.

As a result of the disclosed method of activating B cells, CABs can be used in a wide range of approaches to present a desired antigen, such as a tumor-associated antigen to T cells. Human CABs are very efficient APCs and stimulate human allogeneic naïve CD4+ and CD8+ T cells. They can also prime autologous naïve and memory T cells specific for viral and tumor antigens in animals and humans. Furthermore, in mice these T cell responses are capable of rescuing from lethal viral infections and regressing established tumors.

*Chlamydia trachomatis* Activated B-Cell Platform

Disclosed herein is a platform for creating activated APCs, wherein the platform comprises: *Chlamydia trachomatis*, or an activating protein, peptide, or fragment thereof; a population of B cells; and an antigen. In one example, the antigen of the antigen-presenting cell is not derived from *Chlamydia* spp. (including *C. trachomatis, C. psittaci* and *C. muridarum*), or from a protein, peptide, or fragment thereof. Also disclosed is a *Chlamydia*-activated B cell (CAB) produced by the methods disclosed herein.

The original B cells used herein can be obtained from a number of sources, including peripheral blood mononuclear cells, bone marrow, lymph node tissue, cord blood, tissue from a site of infection, spleen tissue, and tumors. Any number of B cell lines available in the art can be used with the platforms and methods disclosed herein. In certain embodiments of the methods described herein, B cells can be obtained from a unit of blood collected from a subject using any number of techniques known to the skilled artisan, such as FICOLL™ (copolymers of sucrose and epichlorohydrin that may be used to prepare high density solutions) separation.

The *Chlamydia* spp. (including *C. trachomatis, C. psittaci* and *C. muridarum*) used in the platform and methods disclosed herein can be live, inactivated, or can be a protein or a fragment from *Chlamydia* spp. (including *C. trachomatis, C. psittaci* and *C. muridarum*)

The *Chlamydia* spp. can be a variant of the known species, and still retain the function of imparting the effect disclosed herein. For example, the entire bacteria can be used. Live bacteria do not infect leukocytes and cannot survive in an antibiotic-containing culture medium. Alternatively, inactivated whole bacteria (X-ray or gamma-irradiated), or lysate generated from the whole bacteria, can be used.

In another embodiment, specific proteins or fragments thereof which have been identified as being able to activate CABs can be used. By an "activating" protein, peptide, or fragment thereof is meant that the protein, peptide, or fragment thereof is capable of creating activated, antigen-presenting cells (APCs). One of skill in the art can readily identify which proteins, peptides, or fragments thereof of *Chlamydia* is capable of producing the desired result.

Examples of such components that can mediate the effect on B cells include, but are not limited to, major outer membrane protein (MOMP); *Chlamydia trachomatis* polymorphic membrane proteins (e.g. PmpA, PmpB, PmpC, PmpD, PmpE, PmpF, PmpG, PmpH, PmpI); *Chlamydia* protein associating with death domains (CADD); Chlamydial protease-like activity factor (CPAF); Major outer membrane protein and cysteine-rich proteins (e.g. OmcA and OmcB); *Chlamydia trachomatis* 70-kDa heat shock protein; PulD/YscC; PorB; CTL0887; CTLO541; OprB; OMP85; CTL0645; Pal; Ef-Tu/TufA; GroEL; CopD: DnaK/HSP70; CTL0255; Hc1; CTL0850; and RpoB. Further disclosed are Chlamydiae components as found in Heinz et al. (Comprehensive in silico Prediction and Analysis of Chlamydial Outer Membrane Proteins Reflects Evolution and Lifestyle of the Chlamydiae. BMC Genomics. 2009 Dec. 29; 10:634), herein incorporated by reference in its entirety for its discussion of *Chlamydia* proteins.

In one specific embodiment, *Chlamydia trachomatis* major outer membrane protein (MOMP) or a fragment thereof can be used. One of skill in the art can readily determine which fragment, protein, or variant of *Chlamydia* can be used to impart the desired effect.

Any antigen from any disease, disorder, or condition may be used. Exemplary antigens include but are not limited to bacterial, viral, parasitic, allergens, autoantigens and tumor-associated antigens. If a DNA based vaccine is used the antigen will typically be encoded by a sequence of the administered DNA construct. Alternatively, if the antigen is administered as a conjugate the antigen will typically be a protein comprised in the administered conjugate. Particularly, the antigen can include protein antigens, peptides, whole inactivated organisms, and the like.

Specific examples of antigens that can be used include, but are not limited to, antigens from hepatitis A, B, C or D, influenza virus, *Listeria, Clostridium botulinum*, tuberculosis, tularemia, Variola major (smallpox), viral hemorrhagic fevers, *Yersinia pestis* (plague), HIV, herpes, papilloma virus, and other antigens associated with infectious agents. Other antigens include antigens associated with autoimmune conditions, inflammatory conditions, allergy, asthma, and transplant rejection. An antigen-loaded CAB can be administered alone or in conjunction with other therapeutic agents, such as a CD40 agonist or TLR in particular, a CD40 antibody, for use as a therapeutic or prophylactic vaccine for treating a disease condition or for suppressing immunity. In another example, the CAB platform disclosed herein can be used in conjunction with checkpoint inhibitors. Examples of checkpoint inhibitor technology can be found in WO1999015157A2, WO2015016718A1, and WO2010149394A1, which are hereby incorporated in their entireties for their disclosure concerning checkpoint inhibitors. Other combination therapies are discussed herein as well.

In one embodiment, the antigen can comprise a tumor-related antigen. Examples of tumors that can be treated include the following: pancreatic tumors, such as pancreatic ductal adenocarinomas; lung tumors, such as small and large cell adenocarcinomas, squamous cell carcinoma, and bronchoalveolar carcinoma; colon tumors, such as epithelial adenocarcinoma and their metastases; and liver tumors, such as hepatoma and cholangiocarcinoma. Also included are breast tumors, such as ductal and lobular adenocarcinoma; gynecologic tumors, such as squamous and adenocarcinoma of the uterine cervix, and uterine and ovarian epithelial adenocarcinoma; prostate tumors, such as prostatic adenocarcinoma; bladder tumors, such as transitional squamous cell carcinoma; tumors of the RES system, such as nodular or diffuse B or T cell lymphoma, plasmacytoma, and acute or chronic leukemia; skin tumors, such as malignant melanoma; and soft tissue tumors, such as soft tissue sarcoma and leiomyosarcoma. Of especial interest are brain tumors, such as astrocytoma, oligodendroglioma, ependymoma, medulloblastomas, and primitive neural ectodermal tumor. Included in this category are gliomas, glioblastomas, and gliosarcomas.

Specifically, the following antigens are associated with the following types of cancer, and can be used in the platforms and methods disclosed in Table 1:

TABLE 1

| Cancers and Associated Antigens | |
|---|---|
| Melanoma | Tyrosinase, Tyrosinase-related protein (Trp-1), gp100, Melan/MART-1 |
| Prostate adenocarcinoma | Prostate-specific membrane antigen, Prostate-specific acid phosphatase, Prostate specific antigen |
| Pancreatic, lung, breast and colon adenocarcinoma | MUC1 |
| Non-small-cell lung carcinoma | MUC1, MAGE antigens, EGFR |
| Cancer/testis antigens | LAGE/NY-ESO1, MAGE antigens, CEA, AFP |
| Breast cancer | HER-2 |
| Acute myelogenous leukemia | Aurora-A kinase, BRAP, Cyclin A1, hTert, WT1 |
| Chronic lymphocytic leukemia | ROR1 |
| Chronic myelogenous leukemia | BCR/ABL, BRAP, CML28, CML66, PR1, Proteinase 3, survivin, WT1 |

The immune status of the individual may be any of the following: The individual may be immunologically naïve with respect to certain tumor-associated antigens present in the composition, in which case the compositions may be given to initiate or promote the maturation of an anti-tumor response. The individual may not currently be expressing anti-tumor immunity, but may have immunological memory, particularly T cell memory relating to a tumor-associated antigen comprised in the vaccine, in which case the compositions may be given to stimulate a memory response. The individual may also have active immunity (either humoral or cellular immunity, or both) to a tumor-associated antigen comprised in the vaccine, in which case the compositions may be given to maintain, boost, or maturate the response, or recruit other arms of the immune system. The subject should be at least partly immunocompetent, so that the vaccine can induce endogenous T cell responses.

In another embodiment, the antigen can comprise an infectious agent. Examples of infectious agents which can be treated using the platforms and methods disclosed herein include, but are not limited to, Influenza viruses, Respiratory Syncytial Virus (RSV), Human Papilloma Virus (HPV), Hepatitis B Virus (HBV), Hepatitis C Virus (HCV), Human T-Lymphotropic Virus Type-1, Human Immunodeficiency Virus 1 (HIV), Epstein-Barr Virus (EBV), Cytomegalovirus and other Herpesviridae. Other examples include *Listeria monocytogenes, Salmonella, Mycobacterium tuberculosis, Plasmodium* sp. (Malaria), *Toxoplasma gondii*, and *Trypanosoma cruzi*. Specifically, it has been shown that CABs can be used to immunize mice and protect them against ocular infection with HSV-2 (Herpesviridae), which in mice is a lethal infection.

The CABs disclosed herein can be exposed or crosslinked to more than one antigen simultaneously, or sequentially. For example, the CABs disclosed herein can be exposed to 2, 3, 4, 5, 6, or more antigens simultaneously or sequentially, or CABs loaded with different single antigens can be combined together for administration.

The CABs disclosed herein can be significantly expanded as compared to a population of B cells not exposed to *Chlamydia* spp. (including *C. trachomatis, C. psittaci* and *C. muridarum*) or a protein or fragment thereof. As used herein expansion of B cells includes stimulation of proliferation of the cells as well as prevention of apoptosis or other death of the cells. As used herein, "culturing" and "incubation" are used to indicate that the cells are maintained in cell culture medium for a period of time with the appropriate additives (feeder cells, cytokines, agonists, other stimulatory molecules or media, which may include buffers, salts, sugars, serum or various other constituents). Those of skill in the art will appreciate that the culturing or incubation time may be varied to allow proper expansion, to adjust for different cell densities or frequencies of individual subsets, and to allow an investigator to properly time use of the cells. Thus the precise culture length may be determined empirically by one of skill in the art.

The CABs can have higher major histocompatibility complex (MHC) and and/or costimulatory molecule expression levels compared to inactive or resting B cells. For example, the CABs can have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 90, 100% higher MHC and/or costimulatory molecule expression level compared to inactive B cells, or to B cells which have not been exposed to *Chlamydia* spp. (including *C. trachomatis, C. psittaci* and *C. muridarum*) or a protein or fragment thereof. The CABs can have 2, 3, 4, 5, 6, 7, 8, 9, 10, 11, 12, 13, 14, 15, 16, 17, 18, 19, 20, or more fold higher MHC and costimulatory molecule expression level compared to inactive B cells, or to B cells which have not been exposed to *Chlamydia* spp. (including *C. trachomatis, C. psittaci* and *C. muridarum*) or a protein or fragment thereof.

The CABs can have improved capacity to present antigen and activate T cells as compared to inactive B cells. By "improved capacity" is meant that they have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 90, or 100% more capacity to present antigen and activate T cells compared to a population of cells which have not been exposed to *Chlamydia* spp. (including *C. trachomatis, C. psittaci* and *C. muridarum*) or a protein or fragment thereof. The CABs can have 2, 3, 4, 5, 6, 7, 8, 9, 10, 11, 12, 13, 14, 15, 16, 17, 18, 19, 20, or more fold capacity to present antigen and activate T cells compared to a population of cells which have not been exposed to *Chlamydia* spp. (including *C. trachomatis, C. psittaci* and *C. muridarum*) or a protein or fragment thereof.

The CABs can migrate to secondary lymphoid organs at a greater rate than inactive B cells, or B cells which have not been exposed to *Chlamydia* spp. (including *C. trachomatis, C. psittaci* and *C. muridarum*) or a protein or fragment thereof. For example, the CABs can migrate at a rate of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 90, or 100% faster when compared to a population of cells which have not been exposed to *Chlamydia* spp. (including *C. trachomatis, C. psittaci* and *C. muridarum*) or a protein or fragment thereof. The CABs can migrate at a rate which is 2, 3, 4, 5, 6, 7, 8, 9, 10, 11, 12, 13, 14, 15, 16, 17, 18, 19, 20, or more fold compared to a population of cells which have not been exposed to *Chlamydia* spp. (including *C. trachomatis, C. psittaci* and *C. muridarum*) or a protein or fragment thereof.

The CABs can secrete cytokines to enhance T cell recruitment at a greater rate than inactive B cells. For example, the CABs can recruit T-cell enhancement by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 90, or 100% greater rate when compared to a population of cells which have not been exposed to *Chlamydia* spp. (including *C. trachomatis, C. psittaci* and *C. muridarum*) or a protein or fragment thereof. The CABs enhance T cell recruitment at a rate 2, 3, 4, 5, 6, 7, 8, 9, 10, 11, 12, 13, 14, 15, 16, 17, 18, 19, 20, or more fold compared to a population of cells which have not been exposed to *Chlamydia* spp. (including *C. trachomatis, C. psittaci* and *C. muridarum*) or a protein or fragment thereof.

The CABs disclosed herein can have their activity further enhanced by contacting them with a B cell activating factor, e.g., any of a variety of cytokines, growth factors or cell lines known to activate and/or differentiate B cells (see e.g., Fluckiger, et al. Blood 1998 92: 4509-4520; Luo, et al., Blood 2009 1 13: 1422-1431). Such factors may be selected from the group consisting of, but not limited to, IL-1, IL-2, IL-3, IL-4, IL-5, IL-6, IL-7, IL-8, IL-9, IL-10, IL-1 1, IL-12, IL-13, IL-14, IL-15, IL-16, IL-17, IL-18, IL-19, IL-20, IL-21, IL-22, IL-23, IL-24, IL25, IL-26, IL-27, IL-28, IL-29, IL-30, IL-31, IL-32, IL-33, IL-34, and IL-35, IFN-γ, IFN-α, IFN-β, IFN-δ, C type chemokines XCL1 and XCL2, C-C type chemokines and CXC type chemokines, and members of the TNF superfamily {e.g., TNF-α, 4-1 BB ligand, B cell activating factor (BLyS), FAS ligand, sCD40L (including multimeric versions of sCD40L; e.g., histidine-tagged soluble recombinant CD40L in combination with anti-poly-histidine mAb to group multiple sCD40L molecules together), Lymphotoxin, OX40L, RANKL, TRAIL), CpG, and other Toll like receptor agonists (e.g., CpG).

In one embodiment, in particular, CABs can be contacted or cultured on feeder cells. In other embodiments, the culture system described herein is carried out in the absence of feeder cells, providing advantages over other systems known in the art that require feeder cells. Where feeder cells may be used, the feeder cells are a stromal cell line, e.g., the murine stromal cell lines S17 or MS5. In a further embodiment, purified CD19+ cells may be cultured in the presence of fibroblasts expressing CD40-ligand in the presence of B cell activating factor cytokines such as IL-10 and IL-4. CD40L may also be provided bound to a surface such as tissue culture plate or a bead. In another embodiment, purified B cells may be cultured in the presence or absence of feeder cells, with CD40L in presence of one or more cytokines or factors selected from IL-10, IL-4, IL-7, p-ODN, CpG DNA, IL-2, IL-15, IL6, IFN-α, and IFN-δ.

In another embodiment, B cell activating factors may be provided by transfection into the B cell or other feeder cell, such as disclosed in PCT/US2000/030426, herein incorporated by reference in its entirety for its teaching concerning CD40L and B cells. In this context, one or more factors that promote differentiation of the B cell into an antibody secreting cell and/or one or more factors that promote the longevity of the antibody producing cell may be used. Such factors include, for example, Blimp-1, TRF4, anti-apoptotic factors like Bcl-xl or Bcl5, or constitutively active mutants of the CD40 receptor. Further, factors which promote the expression of downstream signaling molecules such as TNF receptor-associated factors (TRAFs) may also be used in the activation/differentiation of the B cells. In this regard, cell activation, cell survival, and antiapoptotic functions of the TNF receptor superfamily are mostly mediated by TRAF1-6 (see e.g., R. H. Arch, et al., Genes Dev. 12 (1998), pp. 2821-2830). Downstream effectors of TRAF signaling include transcription factors in the NF-κB and AP-1 family which can turn on genes involved in various aspects of cellular and immune functions. Further, the activation of NF-κB and AP-1 has been shown to provide cells protection from apoptosis via the transcription of antiapoptotic genes.

The platform can be carried out either ex vivo or in vivo, in whole or in part. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context. For example, the cells can be exposed to an inactivated *Chlamydia* spp. (including *C. trachomatis. C. psittaci* and *C. muridarum*) or peptide or fragment thereof in vivo, or to a live or inactivated *Chlamydia* spp. (including *C. trachomatis, C. psittaci* and *C. muridarum*) or peptide thereof ex vivo, which method is described in more detail herein. The expanded B cells are then exposed or crosslinked to an antigen so that they may differentiate accordingly. Again, this can take place in vivo or ex vivo. For example, the antigen may be directly injected into a subject, or B cells of the subject can be exposed or crosslinked to the modified antigen in vitro (ex vivo), with the expanded, differentiated B cells then returned to the subject. The CABs can be used, for example, in direct in vivo administration, ex vivo somatic therapy, in vivo implantable devices and ex vivo extracorporeal devices.

Vaccines and Methods of Treatment

Also disclosed herein is a method of treating a subject in need thereof, the method comprising: a) obtaining B cells from the subject; b) exposing the B cells from step a) to *Chlamydia trachomatis*, or an activating protein, peptide, or fragment thereof; c) exposing the B cells of step b) to an antigen, wherein the antigen is not derived from *Chlamydia* spp. (including *C. trachomatis, C. psittaci* and *C. muridarum*), or from a protein, peptide, or fragment thereof, thereby obtaining activated, antigen-presenting *Chlamydia*-activated B cells (CABs); and d) treating the subject with the activated, antigen-presenting *Chlamydia*-activated B cells of step c).

The subject being treated can have a variety of diseases or disorders. Any disease or disorder which can be treated using activated B cells can be treated using the methods disclosed herein. For example, infectious diseases and cancer can be treated using these methods.

Also disclosed is a vaccine comprising the *Chlamydia*-activated B cells disclosed herein. Disclosed herein is a cell-based vaccine for ex vivo immunization, as well as compositions and methods for in vivo immunization to elicit an immune response directed against an antigen. In one embodiment, disclosed is a subject with a type of cancer which expresses a tumor-specific antigen. This can result in an improved therapeutic outcome for the patient, evidenced by, e.g., a slowing or diminution of the growth of cancer cells or a solid tumor which expresses the tumor-specific antigen, or a reduction in the total number of cancer cells or total tumor burden. In a related embodiment, the patient has been diagnosed as having a viral, bacterial, fungal or other type of infection, which is associated with the expression of a particular antigen, e.g., a viral antigen. This vaccine can result in an improved therapeutic outcome for the patient as evidenced by a slowing in the growth of the causative infectious agent within the patient and/or a decrease in, or elimination of, detectable symptoms typically associated with the particular infectious disease.

When the vaccine is prepared for administration, it can be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" substance is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

The expression vectors, transduced cells, polynucleotides and polypeptides (active ingredients) can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Pharmaceutical formulations containing the therapeutic agents disclosed herein can be prepared by procedures known in the art using well known and readily available ingredients. The therapeutic agents can also be formulated as solutions appropriate for parenteral administration, for instance by intramuscular, subcutaneous or intravenous routes. The pharmaceutical formulations of the therapeutic agents can also take the form of an aqueous or anhydrous solution or dispersion, or alternatively the form of an emulsion or suspension.

The dose given is an amount "effective" in bringing about a desired therapeutic response, be it the stimulation of an immune response, or the treatment of cancer as defined elsewhere in this disclosure. For the pharmaceutical compositions of this invention, effective doses typically fall within the range of about $10^5$ to $10^{11}$ cells. Preferably, between about $10^6$ to $10^{10}$ cells are used; more preferably between about $1\times10^7$ and $2\times10^9$ cells are used. Multiple doses when used in combination to achieve a desired effect each fall within the definition of an effective amount. The doses can be given multiple times a day, or every day, or every other day, or every third day, etc. Additional doses may be given, such as on a monthly or weekly basis, until the desired effect is achieved. Thereafter, and particularly when the immunological or clinical benefit appears to subside, additional booster or maintenance doses may be given as required.

The various components of the cellular vaccine are present in an "effective combination", which means that there are sufficient amounts of each of the components for the vaccine to be effective. Any number of component cells or other constituents may be used, as long as the vaccine is effective as a whole. This will also depend on the method used to prepare the vaccine.

The pharmaceutical compositions may be given following, preceding, in lieu of, or in combination with, other therapies relating to generating an immune response or treating cancer in the subject. For example, the subject may previously or concurrently be treated by surgical debulking, chemotherapy, radiation therapy, checkpoint inhibitors, and other forms of immunotherapy and adoptive transfer. Where such modalities are used, they are preferably employed in a way or at a time that does not interfere with the immunogenicity of the compositions disclosed herein. The subject may also have been administered another vaccine or other composition in order to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines.

Disclosed herein are combination therapies, comprising administration of a cellular vaccine combination described herein in conjunction with another strategy aimed at providing an anti-tumor immunological response. In one combination therapy, the subject is given an intratumor implant of stimulated allogeneic lymphocytes, either before, during, or after treatment at a site distant from the tumor with a composition comprising the antigen-loaded CABs disclosed herein. In another combination therapy, the subject is treated at sites distant from the tumor with an alternative cellular vaccine composition, either before, during, or after treatment with the antigen-loaded CABs disclosed herein. In another combination therapy, the subject is given checkpoint inhibitors. Where a plurality of different compositions or modes of administration are employed throughout the course of therapy, the order and timing of each element of treatment is chosen to optimize the immunostimulatory or anti-tumor effect.

Production Methods Disclosed herein is a method for producing activated, antigen-presenting *Chlamydia*-activated B cells in a subject, the method comprising: a) obtaining B cells from a subject; b) exposing the B cells from step a) to *Chlamydia trachomatis*, or an activating protein, peptide, or fragment thereof; and c) exposing the B cells of step b) to a desired antigen, wherein the antigen is not derived from *Chlamydia* spp. (including *C. trachomatis. C. psittaci* and *C. muridarum*) or from a protein, peptide, or fragment thereof, thereby obtaining activated, antigen-presenting *Chlamydia*-activated B cells (CABs).

Any of a variety of culture media may be used in the present methods as would be known to the skilled person (see e.g., Current Protocols in Cell Culture, 2000-2009 by John Wiley & Sons, Inc.). In one embodiment, media for use in the methods described herein includes, but is not limited to modified Dulbecco medium (with or without fetal bovine or other appropriate serum). Illustrative media also includes, but is not limited to, IMDM, RPMI 1640, AIM-V, DMEM, MEM, a-MEM, F-12, X-Vivo 15, and X-Vivo 20. In further embodiments, the medium may comprise a surfactant, an antibody, plasmanate or a reducing agent (e.g. N-acetylcysteine, 2-mercaptoethanol), or one or more antibiotics. In some embodiments, IL-2, IL-6, IL-10, soluble CD40L and a cross-linking enhancer may also be used. B cells may be cultured under conditions and for sufficient time periods to achieve activation desired. In certain embodiments, the B cells are cultured under conditions and for sufficient time periods such that 10%, 15%, 20%, 25%, 30%, 35%, 40%, 45%, 50%, 55%, 60%, 65%, 70%, 75%, 80%, 85%, 90%, 95%, or even 100% of the B cells are activated as desired.

In one example, CABs can be generated by using a negative immunomagnetic selection system or RosetteSep™ system to deplete all cell types except $CD4^+$ T cells and B cells from PBMC or whole blood. Selected cells are cultured in the presence of *Chlamydia* spp. and IL-2 (with cell passages every 1-5 days (preferably every 2-3 days) that replenishes media containing *Chlamydia* spp. and IL-2), until adequate numbers of CABs are produced for use with the methods herein. At the time of harvest for use, flow cytometric evaluation of $CD4^+$ T cell frequency can be used to determine if further immunomagnetic selection is needed for further $CD4^+$ T cell depletion.

The induction of B cell activation may be measured by techniques such as $^3$H-thymidine incorporation, which measures DNA synthesis associated with cell proliferation, or by flow cytometric assays using fluorescent markers such as carboxyfluorescein succinimidyl ester. For optimal measurement of B cell proliferation, IL-2 or IL-4 may be added to the culture medium at appropriate concentrations. Alternatively, B cell activation may be measured as a function of immunoglobulin secretion.

After culture for an appropriate period of time, such as from 2, 3, 4, 5, 6, 7, 8, 9, or more days, generally around 3 days, an additional volume of culture medium may be added.

Supernatant from individual cultures may be harvested at various times during culture and quantitated for IgM and IgG1 as described in Noelle et al., (1991) J. Immunol. 146:1 1 18-1 124. In further embodiments, enzyme-linked immunosorbent assay (ELISA) may be used for measuring IgM or other antibody isotype. In certain embodiments, IgG determinations may be made using commercially available antibodies such as goat antihuman IgG, as capture antibody, followed by detection using any of a variety of appropriate detection reagents such as biotinylated goat antihuman Ig, streptavidin alkaline phosphatase and substrate.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Methods of Producing and Using *Chlamydia*-Activated B Cells

B cells to be used with the methods and platform disclosed herein can be obtained from a wide variety of sources including mononuclear cells from peripheral blood, as well as primary and secondary lymphoid organs, such as bone marrow and lymph nodes, respectively. In humans, for example, B cells comprise about 1-15% of total peripheral blood leukocytes, 20-25% of lymph node cells, and up to 50% of splenocytes. If desired, the frequency of B cells can be expanded in vivo, by administration of appropriate cytokines and recruitment growth factors, e.g., IL-4, GM-CSF and 11-3, to the patient prior to obtaining peripheral blood. Mononuclear cells are obtained from these tissues, for example, from peripheral blood through the use of centrifugation through a density gradient, while lymph node cells can be isolated for example, from intact tonsils by mincing the tissue, followed by straining to obtain a single cell suspension. Preferably, mononuclear cells are obtained from peripheral blood. The amount can vary, but about 500 ml of blood can be taken initially from a patient (this can be repeated every eight weeks, for example). Unseparated mononuclear cells from peripheral blood or lymphoid organs in single cell suspensions are cultured in FBS-supplemented RPMI 1640 medium containing additional pyruvate, L-glutamine, non-essential amino acids and antibiotics or in serum-free media (e.g. X-VIVO™ 20) supplemented with antibiotics. To generate CABs, bulk mononuclear cells can be cultured with either inactivated *C. trachomatis* EB, purified as understood by those skilled in the art, or lysates from *C. trachomatis* EB, generated using the commercially available BugBuster@ Protein Extraction Reagent. All tested *Chlamydia* spp. (including *C. trachomatis* [oculogenital strains such as D and E, as well as lymphogranuloma venereum strains such as L2 ], *C. psittaci* and *C. muridarum*), show the same effectiveness at activating resting mammalian B cells. Cells are cultured with *C. trachomatis* in complete medium with no additional manipulation or cytokine supplementation. After 3 days of culture, total cells can be cryopreserved for later use or cultured for 4 to 6 days after the initial addition of *C. trachomatis*, if fresh warm media is provided on day 3 (it is not necessary to provide additional *C. trachomatis* EB at this point), for immediate use. The use of these conditions result in the proliferation and activation of B cells, with no proliferation of T cells. Interestingly, when whole *C. trachomatis*-stimulated cells are cryopreserved after 3 days and later thawed and put in culture again with fresh warm media, CABs start proliferating again overnight.

By appropriate selection of the antigen and the APC, one can promote desired immune responses. Fresh or cryopreserved CABs can be pulsed with the desired antigen one day before use if a whole protein antigen (including cell lysates) is to be used or a few hours before use if a peptide is to be used. Alternatively, transfection of the desired antigens can be performed by transfection of RNA or infection of CAB with viral vectors (e.g. adenoviral or retroviral vectors). On the other hand, CAB can further increase their APC activity through the addition of various factors delivered, either separately or concomitantly, such as loading or crosslinking of CABs with type I NKT cell-activating glycosphingolipids (e.g. alpha-galactosylceramide), type II NKT cell-activating phospholipids or lysophospholipid (e.g. lysophosphatidylethanolamine), and/or gammadelta T cell-activating bisphosphonates (e.g. zoledronic acid) in addition to the antigen of interested. Transfection and infection with vector can also be used to induce expression by CABs of a variety of cytokines, costimulatory factors, or other proteins including anticancer agents, in order to increase their in vivo activity.

After antigen loading and any other desired manipulation, CAB can be prepared for use. If peripheral blood mononuclear cells (PBMC) are used as the source of mononuclear cells, immunomagnetic separation of the cells is necessary before use, as CAB will only represent up to 50% to the obtained cell population after 4-6 days of culture. A custom EasySep™ human B cell enrichment kit without CD2 and CD43 depletion can be used for this purpose, with which >95% CAB is obtained with no detectable T cells, monocytes or DC. However, any similar commercially available immunomagnetic selection system should be suitable. If lymphoid organs were used as the source of mononuclear cells, the initial high frequency of B cells (25-50% of total cells) and the strong stimulation they receive from *C. trachomatis* make the cultures >95% CAB after 4-6 days, with no need for further purification of CAB before use. Thereafter, generated autologous CAB can be administered to the selected patient using multi-administration protocols. CAB can be administered to the patient by any suitable means, including, for example, intravenous infusion, bolus injection, and site directed delivery via a catheter or other means. Due to their amenability to cryopreservation, CAB can be administered immediately after production or potentially several years later if desired.

Example 2

Methods of Conjugating Antigens to *Chlamydia*-Activated B Cells

CABs were produced as indicated in Example 1. Fresh or cryopreserved CABs can be conjugated or crosslinked with the desired antigen (protein or peptide) right before administration to the subject. Conjugation or crosslinking can be performed, for example, using the zero-length crosslinker 1-ethy1-3-(3-dimethylaminopropy1)-carbodiimide (EDAC). CABs are washed with PBS (pH 6.0) and resuspended at $2\times10^8$/ml, then EDAC is added to the cell suspension, followed by the addition of the antigen (protein or peptide) at an adequate concentration, mixed thoroughly and incubated for 1 hour at 4° C. After incubation, antigens crosslinked cells are washed with PBS (pH 7.4) and can undergo further processing or can be prepared for administration. This process can be performed regardless of the source of CABs (autologous or allogeneic). It is possible to use other types of crosslinkers depending on the nature of the antigen (protein, peptide, nucleic acid, lipid or carbohydrate) and the compatibility of the crosslinker with live mammalian cells. FIG. 12 shows the use of crosslinkers.

CAB can further increase their APC activity through the addition of various factors delivered, either separately or concomitantly of antigen crosslinking, such as loading or crosslinking of CABs with type I NKT cell-activating glycosphingolipids (e.g. alpha-galactosylceramide), type II NKT cell-activating phospholipids or lysophospholipid (e.g. lysophosphatidylethanolamine), and/or gamma delta T cell-activating bisphosphonates (e.g. zoledronic acid) in addition to the antigen of interested. Transfection and infection with vector can also be used to induce expression by CABs of a variety of cytokines, costimulatory factors, or other proteins including anticancer agents, in order to increase their in vivo activity.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An ex vivo or in vitro platform for creating a cellular vaccine comprising activated, antigen-presenting cells (APCs) against an antigen of interest, wherein the platform comprises:

a. a whole, inactivated *Chlamydia* spp. bacterium;

b. a population of B cells; and c. the antigen of interest, wherein the antigen is not derived from a *Chlamydia* spp.;

wherein the population of B cells are exposed to the whole, inactivated *Chlamydia* spp. bacterium, thereby forming *Chlamydia*-activated B cells (CABs); wherein said CABs are then exposed or crosslinked to the antigen of interest, thereby forming a cellular vaccine comprising APCs.

2. The platform of claim 1, wherein the *Chlamydia* spp. comprises *C. trachomatis, C. psittaci* or *C. muridarum.*

3. The platform of claim 1, wherein the platform comprises more than one antigen.

4. The platform of claim 3, wherein the platform comprises more than two antigens.

5. The platform of claim 1, wherein the antigen of step c) comprises a tumor-related antigen.

6. The platform of claim 1, wherein the antigen of step c) comprises an infectious agent.

* * * * *